United States Patent [19]

Aliverti et al.

[11] Patent Number: 5,122,376
[45] Date of Patent: Jun. 16, 1992

[54] CALCITONIN GENE RELATED PEPTIDE

[75] Inventors: Valerio Aliverti, Varese; Luciano Dorigotti, Milan; Teodoro Fonio, Milan; Mario Pinza, Milan, all of Italy

[73] Assignee: ISF Societa per Azioni, Italy

[21] Appl. No.: 521,288

[22] Filed: May 9, 1990

[30] Foreign Application Priority Data

May 12, 1989 [IT] Italy ............... 20486 A/89

[51] Int. Cl.$^5$ ............... A01N 25/02; A01N 25/28; A61K 9/16; A61K 37/02
[52] U.S. Cl. ............... 424/405; 424/497; 424/43; 514/946; 514/970; 530/307; 930/60
[58] Field of Search ............... 424/405, 497, 43; 514/970, 946; 530/307; 930/60

[56] References Cited

U.S. PATENT DOCUMENTS

| | | | |
|---|---|---|---|
| 3,988,309 | 10/1976 | Matsuda et al. | 530/307 |
| 4,278,657 | 7/1981 | Tezuka | 514/938 |
| 4,294,829 | 10/1981 | Suzuki et al. | 514/653 |
| 4,304,692 | 12/1981 | Hughes et al. | 525/54.11 |
| 4,393,200 | 7/1983 | Miyashita et al. | 536/18.1 |
| 4,476,116 | 10/1984 | Anik | 514/15 |
| 4,481,187 | 11/1984 | Kondo | 514/970 |
| 4,530,838 | 7/1985 | Evans et al. | 514/11 |
| 4,548,922 | 10/1985 | Carey et al. | 514/4 |
| 4,549,986 | 10/1985 | Evans et al. | 530/324 |
| 4,597,900 | 7/1986 | Orlowski et al. | 530/307 |
| 4,652,441 | 3/1987 | Okada | 424/DIG. 15 |
| 4,711,782 | 12/1987 | Okada | 514/963 |
| 4,835,142 | 5/1989 | Suzuki | 514/180 |
| 4,917,893 | 4/1990 | Okada | 424/497 |

FOREIGN PATENT DOCUMENTS

| | | |
|---|---|---|
| 37943B | 10/1981 | European Pat. Off. |
| 94157 | 11/1983 | European Pat. Off. |
| 127535 | 5/1984 | European Pat. Off. |
| 115627A | 8/1984 | European Pat. Off. |
| 122036 | 10/1984 | European Pat. Off. |
| 0156772 | 10/1985 | European Pat. Off. |
| 173990 | 3/1986 | European Pat. Off. |
| 183527 | 6/1986 | European Pat. Off. |
| 187433 | 7/1986 | European Pat. Off. |
| 214898 | 3/1987 | European Pat. Off. |
| 215697 | 3/1987 | European Pat. Off. |
| 272097 | 6/1988 | European Pat. Off. |
| 275457 | 7/1988 | European Pat. Off. |
| 285367 | 10/1988 | European Pat. Off. |
| 2623090 | 5/1989 | France |
| 61-126034 | 6/1986 | Japan |
| 1354535 | 5/1974 | United Kingdom |
| 1490079 | 10/1977 | United Kingdom |
| 1516947 | 7/1978 | United Kingdom |
| 2008403 | 6/1979 | United Kingdom |
| 2042888 | 10/1980 | United Kingdom |
| 2127689 | 4/1984 | United Kingdom |
| 2167296A | 5/1986 | United Kingdom |

OTHER PUBLICATIONS

L. Illum, *Archiv. for Pharmaci og Chemi*, vol. 94, pp. 127–135, 1987.
K. Morimoto et al., *J. Pharm. Pharmacol.*, 37, 134–136, 1985.
Derwent Abstract: 88-045809/07 of Japan 63002932A, published Jan. 7, 1988.
R. Ziegler, G. Holz, W. Steibl & F. Rave, *Acta. Endocrinol.*, Supple (215), 54–55, 1978.
Derwent Abstract 85-320779/51 of Japan 60224616A published Oct. 9, 1985.
Derwent Abstract 85-246152/40 of Japan 60-161924A, published Aug. 23, 1985.
M. Mishima, W. Wakita, M. Nakano, Presentation at International Conference dated Apr. 2, 1987.
M. Mishima, Y. Wakita, M. Nakano, M. Hirota, S, Ikei, M. Akagi-Presentation at Conference Oct. 20-21, 1986.
S. Oakada, M. Mishima, M. Nakano, S. Ikei, M. Akagi, and S. Shibata-Japanese Pharmacological Meeting, Apr. 4, 1988.
M. Mishima et al., *J. Pharmacobio-Dyn*, 10, s-69 (1987).
S. Hirai, T. Yashiki and Mima, *Int. J. Pharmaceutics* 9, 165-172 and 173-184, (1981).
S. Hirai et al., *Diabetes*, vol. 27, No. 3, p. 296, 1978.
Derwent Abstract 82491 D/45 of Japan 56122309, published Sep. 25, 1981.
Derwent Abstract 92092D/50 of Japan 56140924, published Nov. 4, 1981.
K. Morimoto et al., *J. Pharm. Pharmacol.*, vol. 37, p. 759, 1985.
M. R. Gibson, *Lloydia*, vol. 41, No. 4, pp. 348–349 (1978).
E. Azaz & R. Segal, *Pharm. Acta. Helv.*, 55, Nr. 6, pp. 183–186 (1980).
Chem. Abs. 84: 155579d (1976) of A. Otsuka et al., *Yakugaku Zasshi*, 96(2), 203-8, (1976).
R. Segal, E. Touitou & S. Pisanty, Fourth Int. Conf. on Pharmaceutical Technology, Jun. 1986, Paris.
R. Segal and S. Pisanty, *J. Clinical Pharmacy & Therapeutics* 12, 165–171 (1987).
Derwent Abstract: 87-104723/15 of Japan 62051604, published Mar. 6, 1987.
Derwent Abstract: 83-773656 Japan 58140014A published Aug. 19, 1983.
Derwent Abstract: 82-66899E Japan 57106612A published Jul. 12, 1982.
Mishima et al., *J. Pharmacobio-Dyn*, 12, 31-36 (1989).

*Primary Examiner*—Thurman K. Page
*Assistant Examiner*—Carlos Azpuru
*Attorney, Agent, or Firm*—Dara L. Dinner; Stephen Venetianer; Edward T. Lentz

[57] ABSTRACT

Compositions comprising a calcitonin gene related peptide and, as an absorption enhancer, a glycyrrhizinate.

16 Claims, No Drawings

CALCITONIN GENE RELATED PEPTIDE

The present invention relates to novel compositions for the administration of calcitonin gene related peptides (CGRP) and to a novel method of enhancing the absorption of such peptides across mucosal membranes.

Calcitonin gene related peptides are a class of peptides structurally distinct from calcitonin but derived from the same gene as calcitonin. Calcitonin gene related peptides are believed to contain approximately 37 amino acids and, like calcitonin, in the case of the naturally occurring forms, contain a disulphide bridge between cysteine residues. In CGRP, the disulphide bridge is believed to span the 2- and 7-positions of the peptide.

Examples of CGRPs include; the human CGRP (h-CGRP) described in International Patent Application PCT/EP 84/00307 (Publication No. WO 85/01658) and the rat CGRP (r-CGRP) described in European Patent Application No. 85810123 1 (publication No. EP 056772A).

Such peptides are believed to have the structure:

H—A—Cys—B—Thr—Ala—Thr—Cys—Val—Thr—His—Arg—

Leu—Ala—Gly—Leu—Leu—Ser—Arg—Ser—Gly—Gly—C—

Val—Lys—D—Asn—Phe—Val—Pro—Thr—Asn—Val—Gly—

Ser—E—Ala—Phe—NH$_2$ wherein A is Ser, B is Asn, C is Val, D is Asp and E is Glu (as in r-CGRP); or A is Ala, B is Asp, C is Val, D is Asn and E is Lys (as in h-CGRP alpha form); or A is Ala, B is Asn, C is Met, D is Ser and E is Lys (as in h-CGRP beta-form).

Further examples of CGRPs include chicken CGRP (c-CGRP) as described in European Patent application EP 270,376-A:

H—Ala—Cys—Asn—Thr—Ala—Thr—Cys—Val—Thr—His—Arg—Leu—

Ala—Asp—Phe—Leu—Ser—Arg—Ser—Gly—Gly—Val—Gly—Lys—Asn—

Asn—Phe—Val—Pro—Thr—Asn—Val—Gly—Ser—Lys—Ala—Phe—NH$_2$ and the CGRPs described in European Patent application EP 188,400-A, U.S. Pat. No. 4,530,838 and U.S. Pat. No. 4,549,986.

Calcitonin gene related peptides have been proposed for use in the treatment of a variety of disorders, including calcium metabolic disorders, cardiovascular disorders and ulcers; see, for example, EP 056772A and EP 270,376-A.

A considerable and well known problem with the administration of peptides is that they are susceptible to rapid acid- and enzyme-induced degradation when administered orally. For this reason, parenteral administration has been, hitherto, the most widely used means of administration and, in the case of peptides of higher molecular weight, such as the calcitonins, has been the only significant effective means of administration.

It is widely recognised that administration by injection can be both inconvenient and unpleasant for the patient, particularly when the administration has to be repeated at regular intervals for long periods, e.g. in the treatment of post-menopausal osteoporosis with calcitonins. Thus, there has been growing interest in the administration of peptides by more acceptable non-invasive alternative routes, for example in the form of sublingual tablets, suppositories, intrapulmonary powders, intranasal drops, sprays, powders, gels, ointments and inserts (see for example EP 94157 (Takeda), EP 173990 (Teijin), U.S. Pat. No. 4,476,116 (Syntex) and GB 2,042,888 (Teijin).

A significant problem with many peptides, particularly those of higher molecular weights, is that they are only poorly absorbed across biological membranes, e.g. mucosal membranes, and thus the bioavailability of the peptide is often very low. Considerable research has therefore been carried out in order to find methods of improving the trans-epithelial absorption of peptides. One approach is to use an adjuvant or absorption enhancer and there are numerous published reports of compounds which are claimed to have peptide absorption-enhancing properties.

Thus, for example, choline esters (EP 214898), acyl carnitines (Ep 215697), aldoses and glucosamines (Japanese Pat. Appl. No. 61 126034), asCorbates and salicylates (EP 37943), alpha-cyclodextrin (EP 0094157), pyroglutamate esters (EP 173990), chelating agents (U.S. Pat. No. 4,476,116) and various other compounds (EP 183527) have been proposed as absorption enhancers.

It has been reported that a component of liquorice, sodium glycyrrhetinate, can enhance the nasal absorption of insulin (Mishima et al., J. Pharmacobio. Dyn., 10, s-69 (1987). However, the authors of the report demonstrated that sodium glycyrrhetinate is weaker than sodium caprate as an absorption-enhancing agent for insulin.

There are many published reports that surfactants can enhance the absorption of peptides, see for example EP 115627 (Armour), GB 2,127,689 (Sandoz), U.S. Pat. No. 4,548,922 (Carey et al) and Hirai et al., Int. J. Pharm., 9, 165-184, 1981.

However, a recognised problem with surfactant absorption promoters is that they can cause irritation and histolesion at the site of administration. In the case of nasal administration, it has been proposed (see Hirai et, supra) that the ability of a surfactant to enhance absorption arises at least in part from its ability to cause perturbation or disorder of the structural integrity of the nasal mucosa; i.e. the irritation and histolesive activity of the surfactant are directly linked to its ability to enhance absorption.

The problems of irritation, histolesion and, consequently, poor patient tolerability become of great importance when the peptide is administered regularly over a prolonged period.

It is evident, from the high level of continuing research into methods of improving the absorption of peptides, that there remains a need for compositions containing peptides, which can be administered by a route other than the parenteral route, which give rise to adequate blood levels of the peptide, i.e. have good bioavailability, and, importantly, are well tolerated by the patient over a prolonged period.

It has now been found that the 3-(2-O-β-D-glucopyran-uronosyl-alpha-D-glucopyranosiduronic acid) derivative of glycyrrhetinic acid, known as glycyrrhizinic acid, and its salts not only have excellent mucosal membrane absorption-promoting properties but, moreover, do not give rise to the above-mentioned toxicity problems associated with many absorption promoters when administered over a prolonged period.

In a first aspect, therefore, the present invention provides a method of enhancing the absorption of a calcitonin gene related peptide across a mucosal membrane, which method comprises co-administering with the calcitonin gene related peptide an effective amount of an absorption enhancer which is a glycyrrhizinate.

The present invention also provides a pharmaceutical composition comprising a calcitonin gene related peptide; an effective amount of an absorption enhancer which is a glycyrrhizinate and a pharmaceutically acceptable carrier.

The term glycyrrhizinate as used herein is intended to mean both glycyrrhizinic acid and its carboxylate salts. Particular glycyrrhizinate salts are ammonium glycyrrhizinate and the alkali metal salts e.g. sodium glycyrrhizinate. A preferred salt is ammonium glycyrrhizinate.

The term calcitonin gene related peptide (CGRP) as used herein is intended to refer not only to naturally occurring CGRPs but also to synthetic analogues wherein one or more amino acids have been replaced, reversed or derivatised, or where certain amino acids have been deleted or inserted as described in International Patent applications (e.g.: E.P. 212,432A; JP 63 258,490A; EP 270,376A), for instance:

Preferred calcitonin gene related peptides are h-CGRP and its carbaanalogues.

The compositions of the present invention suitably can be administered by methods known in the art for trans-mucosal delivery of pharmacologically active substances. The compositions can be administered to, for example, the nasal, sublingual, buccal, rectal and vaginal mucosa and can take the form of drops, aerosols, tablets, powders, gels, ointments, inserts, suppositories, pessaries, patches and membranes. The compositions can also take the form of enterically coated solid oral compositions as described in, for example, EP 127535 (Hadassah Medical Organisation).

Particular compositions are those intended for administration to the nasal mucosa.

When the composition is intended for delivery to the nasal mucosa, particular dosage forms are aerosols, drops and gels. Aerosol formulations typically comprise a solution or fine suspension of the active substance in a physiologically acceptable aqueous or non-aqueous solvent and are usually presented in single or multidose quantities in sterile form in a sealed container. The sealed container can take the form of a cartridge or refill for use with an atomising device, or it can take the form of a unitary dispensing device such as a single dose nasal inhaler or an aerosol dispenser fitted with a metering valve and which is intended for disposal once the contents of the container have been exhausted. Where the dosage form comprises an aerosol dispenser, it will contain a propellant which can be a compressed gas such as compressed air or an organic propellant such as a fluorochlorohydrocarbon. Such aerosol dispensers are well known in the art. The aerosol dosage forms can

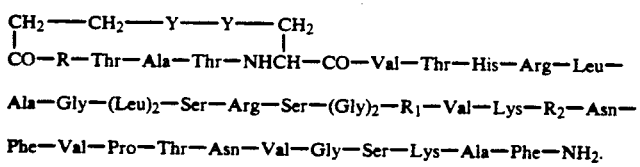

Y=S or CH$_2$
R=Asp or Asn;
R$_1$=Val or Met;
R$_2$=Asn or Ser.

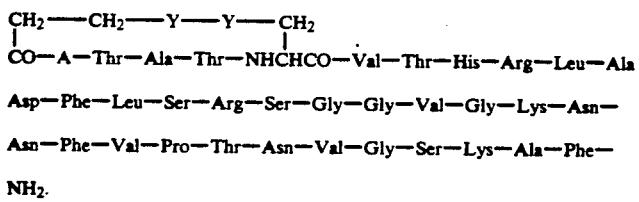

Y=S or CH$_2$
A=Asn or Asp.

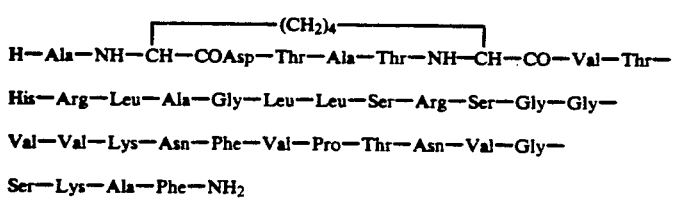

also take the form of a pump-atomiser and such forms are also well known in the art.

The atomising or dispensing devices for dispensing aerosol sprays typically are designed to dispense particles of a size greater than 10μ. In order to ensure that significant quantities of the composition remain in contact with the oral or nasal mucosa, and are not inhaled, the particles suitably are approximately 10–60μ in size.

When the composition is intended to be administered as a liquid spray, the viscosity of the liquid composition will be adjusted as necessary according to known methods to ensure that the composition is sprayable.

The solvents or liquid carriers used in the present formulations are preferably aqueous but can also be chosen from the physiologically acceptable non-aqueous solvents. Examples of non-aqueous solvents or carriers are alcohols, particularly polyhydroxy alcohols such as propylene glycol and glycerol, and vegetable and mineral oils. Such non-aqueous solvents or carriers can be added in various concentrations to water to form solutions, oil-in-water emulsions and water-in-oil emulsions. The solvent preferably is water.

In addition to a solvent or carrier, the liquid formulations of the present invention can contain excipients such as antioxidants, stabilisers, preservatives, agents for adjusting viscosity and tonicity, and buffering agents.

When a preservative is employed, it is chosen such that in the quantities needed to preserve the formulation, it does not cause irritation of the nasal mucosa. This is particularly important when the formulation is intended to be administered on a long term basis. Suitable preservatives are the alkyl p-hydroxyl benzoates (parabens) such as methyl p-hydroxybenzoate and propyl p-hydroxybenzoate. Preferably the preservative does not comprise benzalkonium chloride.

Particular dosage forms for buccal and sublingual administration are gels, suspensions, tablets, patches, powders, ointments and solutions. Particular dosage forms for vaginal and rectal administration include pessaries, suppositories, solutions, foams, suspensions, gels, ointments and tablets.

The above-mentioned compositions can be made according to well known pharmaceutical procedures, see for example Remington's Pharmaceutical Sciences, 17th Edition, Mack Publishing Company, 1985.

When the composition is enterically coated and is intended for oral administration, typically it can take the form of a tablet or capsule coated with a coating agent which ensures passage of the calcitonin gene related peptide through the stomach and its subsequent release in the intestine. Suitable coating agents include anionic polymers such as acrylic acid/methacrylic acid ester copolymers (e.g. Eudragit L, Eudragit S and mixtures thereof).

The compositions of the present invention can be used in the treatment of various cardiovascular disorders, ulcers and calcium metabolic disorders.

The compositions will be administered to the patient in dosages which contain an amount of calcitonin gene related peptide effective to treat the disease in question. The amount administered will depend upon the nature of the disease and its severity and ultimately will be at the discretion of the physician.

The quantity of CGRP in a unit dose of the compositions of the invention will vary according to the potenc of the CGRP and the nature of the composition. However, in general, a unit dose intended for human use typically contains between 1 and 100 mcg of CGRP.

When the formulation is a liquid formulation, particularly a spray, the volume of a unit dose typically is in the rang 50 to 200 mcl.

The pH of the compositions of the present invention can vary within a broad range according to the chemico-physical properties of the different ingredients in the compositions. However, suitably the pH of the composition is in the range from pH 3 to 8, particularly from approximately pH 4.5 to approximately pH 6.

In order to maintain a particular pH value, buffering agents can be used.

Examples of buffering agents are citrates, phosphates or acetates, a particular buffering agent being a mixture of citric acid and sodium citrate.

The concentration of the glycyrrhizinate absorption enhancer typically is at least 0.1% (w/w), suitably 0.5 to 10% (w/w), and preferably 0.5 to 5% (w/w) of the total weight of the composition.

Where the composition is a liquid or gel composition, the glycyrrhizinate suitably is present in an amount corresponding to between 0.5g and 5g per 100ml of composition. Preferably the glycyrrhizinate is present in an amount corresponding to approximately 2g/100 ml.

For aqueous compositions, the final pharmaceutical form, i.e. liquid solution or gel, will depend upon the pH and the ionic strength of the solution containing glycyrrhizinate. In general, compositions having a pH of about 4.5 and above will exist as liquids whilst compositions having a lower pH value will tend to be more viscous and, at around pH 3.5, will exist in a gel form.

The invention will now be illustrated in greater detail by the following examples.

EXAMPLES 1–4

TABLE 1

| | Example No. | | | |
|---|---|---|---|---|
| | 1 | 2 | 3 | 4 |
| h-CGRP (mg) | 1.05 | 1.05 | 1.05 | 1.05 |
| Ammonium glycyrrhizinate (g) | 0.5 | 1 | 2 | 5 |
| Citric acid (mg) | 37 | 37 | 37 | 37 |
| Sodium citrate dihydrate (mg) | 463 | 463 | 463 | 463 |
| Distilled water | q.s. to 100 ml | | | |
| 1N NaOH | q.s. to pH 6 | | | |

The formulations of Examples 1 to 4 are prepared by mixing together the ammonium glycyrrhizinate, citric acid, sodium citrate dihydrate, distilled water and sodium hydroxide in a water bath regulated at a temperature of about 60° C. The resulting solution is allowed to cool to room temperature and the h-CGRP is then added.

EXAMPLES 5–8

TABLE 2

| | Example No. | | | |
|---|---|---|---|---|
| | 5 | 6 | 7 | 8 |
| h-CGRP (mg) | 21.10 | 21.10 | 21.10 | 21.10 |
| Ammonium glycyrrhizinate (g) | 0.5 | 1 | 2 | 5 |
| Citric acid (mg) | 37 | 37 | 37 | 37 |
| Sodium citrate dihydrate (mg) | 463 | 463 | 463 | 463 |
| Distilled water | q.s. to 100 ml | | | |
| 1N NaOH | q.s. to pH 6 | | | |

The formulations of Examples 5 to 8 are prepared by mixing together the ammonium glycyrrhizinate, citric acid, sodium citrate dihydrate, distilled water and sodium hydroxide in a water bath regulated at a temperature of about 60° C. The resulting solution is allowed to cool to room temperature and the h-CGRP is then added.

EXAMPLES 9-12
TABLE 3

|  | Example No. | | | |
| --- | --- | --- | --- | --- |
|  | 9 | 10 | 11 | 12 |
| h-CGRP (mg) | 52.50 | 52.50 | 52.50 | 52.50 |
| Ammonium glycyrrhizinate (g) | 0.5 | 1 | 2 | 5 |
| Citric acid (mg) | 37 | 37 | 37 | 37 |
| Sodium citrate dihydrate (mg) | 463 | 463 | 463 | 463 |
| Distilled water | q.s. to 100 ml | | | |
| 1N NaOH | q.s. to pH 6 | | | |

The formulations of Examples 9 to 12 are prepared by mixing together the ammonium glycyrrhizinate, citric acid, sodium citrate dihydrate, distilled water and sodium hydroxide in a water bath regulated at a temperature of about 60° C. The resulting solution is allowed to cool to room temperature and the h-CGRP is then added.

EXAMPLES 13-16
TABLE 4

|  | Example No. | | | |
| --- | --- | --- | --- | --- |
|  | 13 | 14 | 15 | 16 |
| h-CGRP (mg) | 1.05 | 1.05 | 1.05 | 1.05 |
| Ammonium glycyrrhizinate (g) | 0.5 | 1 | 2 | 5 |
| Citric acid (mg) | 37 | 37 | 37 | 37 |
| Sodium citrate dihydrate (mg) | 463 | 463 | 463 | 463 |
| Methyl p-hydroxybenzoate (mg) | 130 | 130 | 130 | 130 |
| Propyl p-hydroxybenzoate (mg) | 20 | 20 | 20 | 20 |
| Distilled water | q.s. to 100 ml | | | |
| 1N NaOH | q.s. to pH 6 | | | |

The formulations of Examples 13 to 16 are prepared by mixing together the ammonium glydyrrhizinate, citric acid, sodium citrate dihydrate, methyl p-hydroxybenzoate, propyl p-hydroxybenzoate, distilled water and sodium hydroxide in a water bath regulated at a temperature of about 60° C. The resulting solution is allowed to cool to room temperature and the h-CGRP is then added.

EXAMPLES 17-20
TABLE 5

|  | Example No. | | | |
| --- | --- | --- | --- | --- |
|  | 17 | 18 | 19 | 20 |
| h-CGRP (mg) | 21.10 | 21.10 | 21.10 | 21.10 |
| Ammonium glycyrrhizinate (g) | 0.5 | 1 | 2 | 5 |
| Citric acid (mg) | 37 | 37 | 37 | 37 |
| Sodium citrate dihydrate (mg) | 463 | 463 | 463 | 463 |
| Methyl p-hydroxybenzoate (mg) | 130 | 130 | 130 | 130 |
| Propyl p-hydroxybenzoate (mg) | 20 | 20 | 20 | 20 |
| Distilled water | q.s. to 100 ml | | | |
| 1N NaOH | q.s. to pH 6 | | | |

The formulations of Examples 17 to 20 are prepared by mixing together the ammonium glycyrrhizinate, citric acid, sodium citrate dihydrate, methyl p-hydroxybenzoate, propyl p-hydroxybenzoate, distilled water and sodium hydroxide in a water bath regulated at a temperature of about 60° C. The resulting solution is allowed to cool to room temperature and the h-CGRP is then added.

EXAMPLES 21-24
TABLE 6

|  | Example No. | | | |
| --- | --- | --- | --- | --- |
|  | 21 | 22 | 23 | 24 |
| h-CGRP (mg) | 52.50 | 52.50 | 52.50 | 52.50 |
| Ammonium glycyrrhizinate (g) | 0.5 | 1 | 2 | 5 |
| Citric acid (mg) | 37 | 37 | 37 | 37 |
| Sodium citrate dihydrate (mg) | 463 | 463 | 463 | 463 |
| Methyl p-hydroxybenzoate (mg) | 130 | 130 | 130 | 130 |
| Propyl p-hydroxybenzoate (mg) | 20 | 20 | 20 | 20 |
| Distilled water | q.s. to 100 ml | | | |
| 1N NaOH | q.s. to pH 6 | | | |

The formulations of Examples 21 to 24 are prepared by mixing together the ammonium glycyrrhizinate, citric acid, sodium citrate dihydrate, methyl p-hydroxybenzoate, propyl p-hydroxybenzoate, distilled water and sodium hydroxide in a water bath regulated at a temperature of about 60° C. The resulting solution is allowed to cool to room temperature and the h-CGRP is then added.

EXAMPLES 25-27
TABLE 7

|  | Example No. | | |
| --- | --- | --- | --- |
|  | 25 | 26 | 27 |
| h-CGRP (mg) | 1.05 | 21.10 | 52.50 |
| Ammonium glycyrrhizinate (g) | 0.5 | 0.5 | 0.5 |
| Citric acid (mg) | 37 | 37 | 37 |
| Sodium citrate dihydrate (mg) | 463 | 463 | 463 |
| Methyl p-hydroxybenzoate (mg) | 130 | 130 | 130 |
| Propyl p-hydroxybenzoate (mg) | 20 | 20 | 20 |
| Distilled water | q.s. to 100 ml | | |
| 0.1N NaOH | q.s. to pH 4.5 | | |

The formulations of Examples 25 to 27 are prepared by mixing together the ammonium glycyrrhizinate, citric acid, sodium citrate dihydrate, methyl p-hydroxybenzoate, propyl p-hydroxybenzoate, distilled water and sodium hydroxide in a water bath regulated at a temperature of about 60° C. The resulting solution is allowed to cool to room temperature and the h-CGRP is then added. The formulations of these Examples are gels.

EXAMPLES 28-31
TABLE 8

|  | Example No. | | | |
| --- | --- | --- | --- | --- |
|  | 28 | 29 | 30 | 31 |
| h-CGRP (mg) | 1.05 | 1.05 | 1.05 | 1.05 |
| Ammonium glycyrrhizinate (g) | 0.5 | 1 | 2 | 5 |
| Citric acid (mg) | 37 | 37 | 37 | 37 |
| Sodium citrate dihydrate (mg) | 463 | 463 | 463 | 463 |
| Methyl p-hydroxybenzoate (mg) | 130 | 130 | 130 | 130 |
| Propyl p-hydroxybenzoate (mg) | 20 | 20 | 20 | 20 |
| Sodium chloride (mg) | 600 | 600 | 600 | 600 |
| Distilled water | q.s. to 100 ml | | | |
| 1N NaOH | q.s. to pH 6 | | | |

The formulations of Examples 28 to 31 are prepared by mixing together the ammonium glycyrrhizinate, citric acid, sodium citrate dihydrate, methyl p-hydroxybenzoate, propyl p-hydroxybenzoate, sodium chloride, distilled water and sodium hydroxide in a water batch regulated at a temperature of about 60° C. The resulting solution is allowed to cool to room temperature and the h-CGRP is then added.

EXAMPLES 32-35

TABLE 9

|  | Example No. | | | |
| --- | --- | --- | --- | --- |
|  | 32 | 33 | 34 | 35 |
| h-CGRP (mg) | 21.10 | 21.10 | 21.10 | 21.10 |
| Ammonium glycyrrhizinate (g) | 0.5 | 1 | 2 | 5 |
| Citric acid (mg) | 37 | 37 | 37 | 37 |
| Sodium citrate dihydrate (mg) | 463 | 463 | 463 | 463 |
| Methyl p-hydroxybenzoate (mg) | 130 | 130 | 130 | 130 |
| Propyl p-hydroxybenzoate (mg) | 20 | 20 | 20 | 20 |
| Sodium chloride (mg) | 600 | 600 | 600 | 600 |
| Distilled water | q.s. to 100 ml | | | |
| 1N NaOH | q.s. to pH 6 | | | |

The formulations of Examples 32 to 35 are prepared by mixing together the ammonium glycyrrhizinate, citric acid, sodium citrate dihydrate, methyl p-hydroxybenzoate, propyl p-hydroxybenzoate, sodium chloride, distilled water and sodium hydroxide in a water bath regulated at a temperature of about 60° C. The resulting solution is allowed to cool to room temperature and the h-CGRP is then added.

EXAMPLES 36-39

TABLE 10

|  | Example No. | | | |
| --- | --- | --- | --- | --- |
|  | 36 | 37 | 38 | 39 |
| h-CGRP (mg) | 52.50 | 52.50 | 52.50 | 52.50 |
| Ammonium glycyrrhizinate (g) | 0.5 | 1 | 2 | 5 |
| Citric acid (mg) | 37 | 37 | 37 | 37 |
| Sodium citrate dihydrate (mg) | 463 | 463 | 463 | 463 |
| Methyl p-hydroxybenzoate (mg) | 130 | 130 | 130 | 130 |
| Propyl p-hydroxybenzoate (mg) | 20 | 20 | 20 | 20 |
| Sodium chloride (mg) | 600 | 600 | 600 | 600 |
| Distilled water | q.s. to 100 ml | | | |
| 1N NaOH | q.s. to pH 6 | | | |

The formulations of Examples 36 to 39 are prepared by mixing together the ammonium glycyrrhizinate, citric acid, sodium citrate dihydrate, methyl p-hydroxybenzoate, propyl p-hydroxybenzoate, sodium chloride, distilled water and sodium hydroxide in a water bath regulated at a temperature of about 60° C. The resulting solution is allowed to cool to room temperature and the h-CGRP is then added.

EXAMPLES 40-41

TABLE 11

|  | Example No. | | | |
| --- | --- | --- | --- | --- |
|  | 40 | 41 | 42 | 43 |
| h-CGRP (mg) | 1.05 | 1.05 | 1.05 | 1.05 |
| Ammonium glycyrrhizinate (g) | 0.5 | 1 | 2 | 5 |
| Citric acid (mg) | 37 | 37 | 37 | 37 |
| Sodium citrate dihydrate (mg) | 463 | 463 | 463 | 463 |
| Methyl p-hydroxybenzoate (mg) | 130 | 130 | 130 | 130 |
| Propyl p-hydroxybenzoate (mg) | 20 | 20 | 20 | 20 |
| Sodium chloride (mg) | 600 | 600 | 600 | 600 |
| Polysorbate 80 (mg) | 5 | 5 | 5 | 5 |
| Distilled water | q.s. to 100 ml | | | |
| 1N NaOH | q.s. to pH 6 | | | |

The formulations of Examples 40 to 43 are prepared by mixing together the ammonium glycyrrhizinate, citric acid, sodium citrate dihydrate, methyl p-hydroxybenzoate, propyl p-hydroxybenzoate, sodium chloride, polysorbate 80, distilled water and sodium hydroxide in a water bath regulated at a temperature of about 60° C. The resulting solution is allowed to cool to room temperature and the h-CGRP is then added.

EXAMPLES 44-47

TABLE 12

|  | Example No. | | | |
| --- | --- | --- | --- | --- |
|  | 44 | 45 | 46 | 47 |
| h-CGRP (mg) | 21.10 | 21.10 | 21.10 | 21.10 |
| Ammonium glycyrrhizinate (g) | 0.5 | 1 | 2 | 5 |
| Citric acid (mg) | 37 | 37 | 37 | 37 |
| Sodium citrate dihydrate (mg) | 463 | 463 | 463 | 463 |
| Methyl p-hydroxybenzoate (mg) | 130 | 130 | 130 | 130 |
| Propyl p-hydroxybenzoate (mg) | 20 | 20 | 20 | 20 |
| Sodium chloride (mg) | 600 | 600 | 600 | 600 |
| Polysorbate 80 (mg) | 5 | 5 | 5 | 5 |
| Distilled water | q.s. to 100 ml | | | |
| 1N NaOH | q.s. to pH 6 | | | |

The formulations of Examples 44 to 47 are prepared by mixing together the ammonium glycyrrhizinate, citric acid, sodium citrate dihydrate, methyl p-hydroxybenzoate, propyl p-hydroxybenzoate, sodium chloride, polysorbate 80, distilled water and sodium hydroxide in a water bath regulated at a temperature of about 60° C. The resulting solution is allowed to cool to room temperature and the h-CGRP is then added.

EXAMPLES 48-51

TABLE 13

|  | Example No. | | | |
| --- | --- | --- | --- | --- |
|  | 48 | 49 | 50 | 51 |
| h-CGRP (mg) | 52.50 | 52.50 | 52.50 | 52.50 |
| Ammonium glycyrrhizinate (g) | 0.5 | 1 | 2 | 5 |
| Citric acid (mg) | 37 | 37 | 37 | 37 |
| Sodium citrate dihydrate (mg) | 463 | 463 | 463 | 463 |
| Methyl p-hydroxybenzoate (mg) | 130 | 130 | 130 | 130 |
| Propyl p-hydroxybenzoate (mg) | 20 | 20 | 20 | 20 |
| Sodium chloride (mg) | 600 | 600 | 600 | 600 |
| Polysorbate 80 (mg) | 5 | 5 | 5 | 5 |
| Distilled water | q.s. to 100 ml | | | |
| 1N NaOH | q.s. to pH 6 | | | |

The formulations of Examples 48 to 51 are prepared by mixing together the ammonium glycyrrhizinate, citric acid, sodium citrate dihydrate, methyl p-hydroxybenzoate, propyl p-hydroxybenzoate, sodium chloride, polysorbate 80, distilled water and sodium hydroxide in a water bath regulated at a temperature of about 60° C. The resulting solution is allowed to cool to room temperature and the h-CGRP is then added.

EXAMPLES 52-55

TABLE 14

|  | Example No. | | | |
| --- | --- | --- | --- | --- |
|  | 52 | 53 | 54 | 55 |
| h-CGRP (mg) | 1.05 | 1.05 | 1.05 | 1.05 |
| Ammonium glycyrrhizinate (g) | 0.5 | 1 | 2 | 5 |
| Citric acid (mg) | 37 | 37 | 37 | 37 |
| Sodium citrate dihydrate (mg) | 463 | 463 | 463 | 463 |
| Methyl p-hydroxybenzoate (mg) | 130 | 130 | 130 | 130 |
| Propyl p-hydroxybenzoate (mg) | 20 | 20 | 20 | 20 |

TABLE 14-continued

|  | Example No. | | | |
| --- | --- | --- | --- | --- |
|  | 52 | 53 | 54 | 55 |
| Sodium chloride (mg) | 600 | 600 | 600 | 600 |
| Polysorbate 80 (mg) | 10 | 10 | 10 | 10 |
| Distilled water | q.s. to 100 ml | | | |
| 1N NaOH | q.s. to pH 6 | | | |

The formulations of Examples 52 to 55 are prepared by mixing together the ammonium glycyrrhizinate, citric acid, sodium citrate dihydrate, methyl p-hydroxybenzoate, propyl p-hydroxybenzoate, sodium chloride, polysorbate 80, distilled water and sodium hydroxide in a water bath regulated at a temperature of about 60° C. The resulting solution is allowed to cool to room temperature and the h-CGRP is then added.

EXAMPLES 56-59

TABLE 15

|  | Example No. | | | |
| --- | --- | --- | --- | --- |
|  | 56 | 57 | 58 | 59 |
| h-CGRP (mg) | 21.10 | 21.10 | 21.10 | 21.10 |
| Ammonium glycyrrhizinate (g) | 0.5 | 1 | 2 | 5 |
| Citric acid (mg) | 37 | 37 | 37 | 37 |
| Sodium citrate dihydrate (mg) | 463 | 463 | 463 | 463 |
| Methyl p-hydroxybenzoate (mg) | 130 | 130 | 130 | 130 |
| Propyl p-hydroxybenzoate (mg) | 20 | 20 | 20 | 20 |
| Sodium chloride (mg) | 600 | 600 | 600 | 600 |
| Polysorbate 80 (mg) | 10 | 10 | 10 | 10 |
| Distilled water | q.s. to 100 ml | | | |
| 1N NaOH | q.s. to pH 6 | | | |

The formulations of Examples 56 to 59 are prepared by mixing together the ammonium glycyrrhizinate, citric acid, sodium citrate dihydrate, methyl p-hydroxybenzoate, propyl p-hydroxybenzoate, sodium chloride, polysorbate 80, distilled water and sodium hydroxide in a water bath regulated at a temperature of about 60° C. The resulting solution is allowed to cool to room temperature and the h-CGRP is then added.

EXAMPLES 60-63

TABLE 16

|  | Example No. | | | |
| --- | --- | --- | --- | --- |
|  | 60 | 61 | 62 | 63 |
| h-CGRP (mg) | 52.50 | 52.50 | 52.50 | 52.50 |
| Ammonium glycyrrhizinate (g) | 0.5 | 1 | 2 | 5 |
| Citric acid (mg) | 37 | 37 | 37 | 37 |
| Sodium citrate dihydrate (mg) | 463 | 463 | 463 | 463 |
| Methyl p-hydroxybenzoate (mg) | 130 | 130 | 130 | 130 |
| Propyl p-hydroxybenzoate (mg) | 20 | 20 | 20 | 20 |
| Sodium chloride (mg) | 600 | 600 | 600 | 600 |
| Polysorbate 80 (mg) | 10 | 10 | 10 | 10 |
| Distilled water | q.s. to 100 ml | | | |
| 1N NaOH | q.s. to pH 6 | | | |

The formulations of Examples 60 to 63 are prepared by mixing together the ammonium glycyrrhizinate, citric acid, sodium citrate dihydrate, methyl p-hydroxybenzoate, propyl p-hydroxybenzoate, sodium chloride, polysorbate 80, distilled water and sodium hydroxide in a water bath regulated at a temperature of about 60° C. The resulting solution is allowed to cool to room temperature and the h-CGRP is then added.

EXAMPLES 64-65

TABLE 17

|  | Example No. | |
| --- | --- | --- |
|  | 64 | 65 |
| c-CGRP (mg) | 0.56 | 20.50 |
| Ammonium glycyrrhizinate (g) | 2 | 2 |
| Citric acid (mg) | 37 | 37 |
| Sodium citrate dihydrate (mg) | 463 | 463 |
| Methyl p-hydroxybenzoate (mg) | 130 | 130 |
| Propyl p-hydroxybenzoate (mg) | 20 | 20 |
| Sodium chloride (mg) | 600 | 600 |
| Distilled water | q.s. to 100 ml | |
| 1N NaOH | q.s. to pH 6 | |

The formulations of Examples 64 to 65 are prepared by mixing together the ammonium glycyrrhizinate, citric acid, sodium citrate dihydrate, methyl p-hydroxybenzoate, propyl p-hydroxybenzoate, sodium chloride, distilled water and sodium hydroxide in a water bath regulated at a temperature of about 60° C. The resulting solution is allowed to cool to room temperature and the c-CGRP is then added.

Powder for nasal administration

EXAMPLES 66-68

TABLE 18

|  | Example No. | | |
| --- | --- | --- | --- |
|  | 66 | 67 | 68 |
| h-CGRP (mg) | 1.05 | 21.10 | 52.50 |
| Ammonium glycyrrhizinate (g) | 2.0 | 2.0 | 2.0 |
| Lactose q.s. to (g) | 25.0 | 25.0 | 25.0 |

The formulations of Examples 66 to 68 are prepared by wetting the lactose with an aqueous solution of h-CGRP and drying under vacuum. The dried powder is mixed with ammonium glycyrrhizinate and the final mixture is placed into hard gelatin capsules (25 mg each capsule). The powder is administered, after having pierced the capsules, using a nasal insufflator.

Sublingual tablets

EXAMPLES 69-71

TABLE 19

|  | Example No. | | |
| --- | --- | --- | --- |
|  | 69 | 70 | 71 |
| h-CGRP (mg) | 2.10 | 21.10 | 52.50 |
| Ammonium glycyrrhizinate (g) | 4.0 | 4.0 | 4.0 |
| Sucrose (g) | 35.0 | 35.0 | 35.0 |
| Mannitol (g) | 35.0 | 35.0 | 35.0 |
| Polyethylene glycol 6000 (g) | 10.0 | 10.0 | 10.0 |
| Lactose q.s. to (g) | 120.0 | 120.0 | 120.0 |

The formulations of Examples 69 to 71 are prepared by mixing together the sucrose, the mannitol and the lactose. The resulting mixture is wetted with an aqueous solution of h-CGRP, granulated through a stainless steel screen and dried under vacuum. The dried granules are mixed with polyethylene glycol and ammonium glycyrrhizinate and then compressed into tablets of 120 mg each.

Oral tablets for colonic delivery

EXAMPLES 72-74

TABLE 20

|  | Example No. | | |
| --- | --- | --- | --- |
|  | 72 | 73 | 74 |
| h-CGRP (mg) | 21.10 | 52.50 | 103.20 |
| Ammonium glycyrrhizinate (g) | 6.0 | 6.0 | 6.0 |
| Pregelatinized starch (g) | 80.0 | 80.0 | 80.0 |
| Magnesium stearate (g) | 2.0 | 2.0 | 2.0 |
| Lactose q.s. to (g) | 210.0 | 210.0 | 210.0 |
| Eudragit S (g) | 20.0 | 20.0 | 20.0 |
| Polyethylene glycol 6000 (g) | 2.0 | 2.0 | 2.0 |

The formulation of Examples 72 to 74 are prepared by mixing together the pregelatinized starch and the lactose. The resulting mixture is wetted with an aqueous solution of h-CGRP, granulated through a stainless steel screen and dried under vacuum. The dried granules are mixed with ammonium glycyrrhizinate and magnesium stearate and then compressed into tablets of 210 mg each.

The tablets are coated with an aqueous suspension of polyethylene glycol and Eudragit, to a final weight of 232 mg/tablet.

EXAMPLE 75

Trial A

The preparation reported in Example 32 containing ammonium glycyrrhizinate 0.5% as absorption enhancer and the preparation reported in Example 34, containing ammonium glycyrrhizinate 2% as absorption enhancer, were compared, on a test of pharmacodynamic activity i.e. lowering of calcium concentration in the serum, with the following preparations:
a formulation containing the same concentration of h-CGRP and the same excipients with the exception of the ammonium glycyrrhizinate (reference preparation A); a formulation containing the same concentration of h-CGRP, benzalkonium chloride 0.01% and citrates as excipients (reference preparation B); a formulation containing the same concentration of h-CGRP, sodium taurocholate 1%, parabens 0.15% and citrates (reference preparation C). The preparations were administered intranasally with a small catheter, in the volume of 10 mcl, to groups of 10 male Sprague Dawley rats weighing 160+10 g. The animals, fasted overnight, were anaesthetized with tribromoethanol (TBE) 2% (0.9 ml/100 g b.w. given i.p.) 15 min before receiving h-CGRP.

Serum calcium concentration was measured (with an atomic absorption spectrophotometer VARIAN 30/40) on blood samples obtained in each animal, from the orbital sinus, 60, 120 and 180 min after administration of the product. Basal values were obtained at the same times in animals fasted and anaesthetized as described above but receiving no treatment. The results are reported in Table 21.

TABLE 21

|  | Administered dosage mcg/kg | Percent decrease of serum calcium as compared with basal values | | |
| --- | --- | --- | --- | --- |
|  |  | 1 h | 2 h | 3 h |
| Preparation of this invention - Reported in example 32 | 13.18 | 15.7 | 10.1 | 0.3 |
| Preparation of this invention - Reported in example 34 | 13.18 | 18.3 | 16.2 | 5.1 |
| Reference preparation A | 13.18 | 8.4 | 3.5 | 1.1 |
| Reference preparation B | 13.18 | 7.8 | 2.1 | 0.1 |
| Reference preparation C | 13.18 | 12.3 | 8.9 | 1.5 |

What is claimed is:

1. A pharmaceutical composition comprising a calcitonin gene related peptide, an effective amount of a glycyrrhizinate absorption enhancer in a concentration of at least 0.1% by weight, and a pharmaceutically acceptable carrier.

2. The composition according to claim 1 wherein the glycyrrhizinate is ammonium glycyrrhizinate.

3. The composition according to claim 1 wherein the glycyrrhizinate is present in a concentration corresponding to 0.5 to 10% (w/w) of the total weight of the composition.

4. The composition according to claim 3 wherein the concentration of glycyrrhizinate is 0.5 to 5% (w/w).

5. The composition according to claim 1 wherein the calcitonin gene related peptide is h-CGRP.

6. The composition according to claim 1 in the form of a liquid or gel suitable for application to the nasal mucosa.

7. The composition according to claim 6 wherein the glycyrrhizinate is present in an amount corresponding to approximately 2 g per 100 ml of composition.

8. The composition according to claim 1 which is packaged for administration as a spray.

9. The composition according to claim 7 which is packaged for administration as a spray.

10. The composition according to claim 1 which has a pH in the range from approximately 4.5 to approximately 6.

11. The composition according to claim 1 wherein the calcitonin gene related peptide is h-CGRP and the glycyrrhizinate is ammonium glycyrrhizinate.

12. The composition according to claim 11 in the form of a liquid suitable for application to the nasal mucosa.

13. The composition according to claim 12 which has a pH in the range from approximately 4.5 to approximately 6 and is packaged for administration as a spray.

14. The composition according to claim 13 wherein the glycyrrhizinate is present in an amount corresponding to approximately 2 g per 100 ml of composition.

15. A method of enhancing the absorption of a calcitonin gene related peptide across a mucosal membrane which method comprises co-administering with the calcitonin gene related peptide an effective amount of a glycyrrhizinate absorption enhancer in a concentration of at least 0.1% by weight.

16. The composition according to claim 1 wherein the glycyrrhizinate is sodium glycyrrhizinate.

* * * * *